United States Patent
Kaully et al.

(10) Patent No.: US 6,669,122 B2
(45) Date of Patent: Dec. 30, 2003

(54) METHOD AND APPARATUS FOR SHAPING PARTICLES BY ULTRASONIC CAVITATION

(75) Inventors: Tamar Kaully, Mitzpe Adi (IL); Benjamin Keren, Misgav (IL); Tamar Kimmel, Caesarea (IL); Orly Dekel, Nesher (IL)

(73) Assignee: Rafael-Armament Development Authority Ltd. (IL)

( * ) Notice: Subject to any disclaimer, the term of this patent is extended or adjusted under 35 U.S.C. 154(b) by 0 days.

(21) Appl. No.: 09/899,639

(22) Filed: Jul. 5, 2001

(65) Prior Publication Data

US 2002/0036244 A1 Mar. 28, 2002

Related U.S. Application Data

(63) Continuation of application No. PCT/IL00/00003, filed on Jan. 3, 2000.

(30) Foreign Application Priority Data

Jan. 11, 1999 (IL) ................................................ 128001

(51) Int. Cl.⁷ ............................................... B02C 19/12
(52) U.S. Cl. .............................. 241/1; 241/21; 241/23; 241/301
(58) Field of Search .................... 204/157.42; 241/1, 241/301, 21, 23

(56) References Cited

U.S. PATENT DOCUMENTS

| | | |
|---|---|---|
| 3,222,231 A | 12/1965 | Markels, Jr. et al. |
| 5,035,363 A | 7/1991 | Somoza |
| 5,395,592 A | 3/1995 | Bolleman et al. |
| 5,471,001 A | 11/1995 | Anderson et al. |

FOREIGN PATENT DOCUMENTS

| | | |
|---|---|---|
| DE | 1 262 240 B | 11/1964 |
| EP | 0 275 607 A1 | 7/1998 |
| GB | 2 276 567 A | 10/1994 |

OTHER PUBLICATIONS

A.F. McIntosh, et al., "Ultrasonic Treatment of Microorganisms", Process Biochemistry, pp. 22–23 & 27, Mar. 1971.
D. Gold, "Ultasonic Sterilization of Pharmaceutical Preparations", Thesis, University of Connecticut Storrs, CT, USA, 1962.
A. van der Steen, "Crystal Quality And Less Sensitive Explosives", Insensitive Munitions Technology Symposium, Jun. 16–18, 1992, Williamsburg, VA, USA.

*Primary Examiner*—Mark Rosenbaum
(74) *Attorney, Agent, or Firm*—Lerner, David, Littenberg, Krumholz & Mentlik, LLP

(57) ABSTRACT

Method of shaping solid, particulate materials, which comprises forming a raw slurry of the starting material, in a liquid which is a partial solvent of said material, and submitting the slurry to treatment by ultrasound generators to produce therein ultrasonic vibrations which shape and grind the starting, particulate material to produce a shaped slurry of ground and shaped particles. The shaped particles may be separated from their slurry by removing the partial solvent by decantation and/or filtration. The partial solvent may be a liquid in which the material to be shaped has a solubility comprised between 1 and 10, wherein the solubility is expressed as grams of material that are dissolved in 100 ml of the liquid at a temperature of 20° C. The partial solvent can be chosen from among acetone, methyl ethyl ketone, and mixtures of said solvents with one another or other solvents and/or a minor amount of water, and may also be an organic solvent.

17 Claims, 5 Drawing Sheets

METHOD AND APPARATUS FOR SHAPING PARTICLES BY ULTRASONIC CAVITATION

CROSS-REFERENCE TO RELATED APPLICATIONS

The present application is a continuation of International Application No. PCT/IL00/00003, filed on Jan. 3, 2000, which was published in English, and the disclosure of which is incorporated by reference herein.

FIELD OF THE INVENTION

This invention relates to method and apparatus for the ultrasonic shaping of particles, particularly of organic compounds, which permit to obtain by ultrasonic cavitation shaped particles having smooth and rounded surfaces. The method and apparatus can produce shaped particles of different sizes and can also grind the particles. Typical, but not exclusive, applications of the invention are the shaping of high explosives, solid propellants, and pharmaceuticals.

BACKGROUND OF THE INVENTION

The use of ultrasonic cavitation has been proposed in the microbiological and pharmaceutical field: thus McIntosh, A. F. and R. F. Munro, in "Ultrasonic Treatment of Microorganism," Process Biochem 6 (3) 22–3, 37 (1971) and Gold D., in "Ultrasonic Sterilization of Pharmaceutical Preparations," 1962, Thesis, University of Connecticut Storrs, Conn. 06268. Ultrasonic cavitation can produce the mechanical disruption of cell membranes.

Ultrasonic cavitation can also be used for grinding solid particulate materials, including even explosives and solid propellants. The state of the art in this respect is summarized in U.S. Pat. No. 5,035,363, the content of which is herein included by reference. One of the known processes for grinding explosives and solid propellants is wet grinding, viz. grinding of a slurry of a solid material in a liquid; and a particular form of wet grinding is ultrasonic grinding, in which a slurry of a solid material in a liquid is subjected to ultrasonic vibrations.

U.S. Pat. No. 5,035,363 discloses an ultrasonic grinding process, which includes suspending the particles to be ground in a liquid to form a slurry and subjecting the slurry to ultrasonic energy at a frequency or frequencies in the range of about 14 to 60 KHz. The liquid medium of the slurry must be inert, viz. not reactive chemically with the explosive material being ground, and must also be a non-solvent as regards said material. The preferred slurry liquid is water or other aqueous liquid medium. The explosives mentioned in said application are cyclotrimethylenetrinitramine (RDX), tetramethylenetetranitramine (HMX) and a mixture of RDX and HMX known as co-produced explosive (CPX).

The apparatus disclosed in said patent comprises an ultrasound generator, including a transducer and a sonic converter, which imparts ultrasonic vibrations to the tip of a disrupter horn. A vessel is provided, into which flows an input stream of a slurry containing the unground explosive particles and out of which flows an output stream of the slurry containing the ground explosive particles. The tip of the disruptor horn is submerged in the slurry and is located so that all particles passing through the apparatus are subjected to a high intensity ultrasonic field below the tip, where the primary acoustic cavitation occurs, the stream of ground particles flowing through an orifice located immediately below the tip of the horn and therefrom to the apparatus outlet. In said patent, however, no consideration is given to the shape of the ground particles and rounded particles are not obtained.

An attempt to improve the crystal shape and surface smoothness of particles of RDX, without changing their size, is described by A. van der Steen et al, in "Crystal Quality and Less Sensitive Explosives," a paper presented at the "Insensitive Munitions Technology Symposium," Jun. 16–18, 1992, Williamsburg, Va. The Authors treated spheroidized RDX particles with saturated acetone and then with unsaturated acetone or ethyl acetate. Smoother surfaces and flattened crystal shapes were thus obtained.

Experience has shown that the shape of the particles is of the highest importance, and more precisely, it is highly desirable that the ground particles have smooth surfaces and a generally rounded shape, approaching a spherical shape. A rounded shape improves the flowability of the particles when they are used in composite paste materials. It permits better packaging, increasing the amount of material that can be packaged in a given space, e.g. providing more solid loading of powder in explosives, solid propellants and other particulate material.

It is a purpose of this application to provide a shaping method and apparatus that permit to shape solid, particulate materials, preferably of organic compounds, in such a way as to obtain particles that have smooth and rounded surfaces and approach a spherical shape.

It is another purpose of this invention to provide such a shaping method and apparatus that are particularly suited for shaping high explosives, solid propellants, or solid pharmaceutical preparations.

It is a further purpose of this invention to provide such a shaping method and apparatus which produce powders of improved flowability and packaging properties.

It is a still further purpose of this invention to provide such a shaping method that is efficient and of limited cost.

It is a still further purpose of this invention to provide such a shaping method that does not produce an uncontrolled reduction of the size of the particles.

It is a still further purpose of the invention to provide such a method and apparatus which, when applied to the shaping of explosives, are secure and do not generate temperatures which exceed a safe limit.

It is a still further purpose of this invention to achieve the aforesaid purposes by a method and apparatus which are simple and inexpensive.

Other purposes and advantages of the invention will appear as the description proceeds.

SUMMARY OF THE INVENTION

The shaping method of the invention comprises forming a raw slurry, viz. a slurry of the starting, particulate material, in a liquid which is a partial solvent of said material, and submitting the slurry to treatment by ultrasound generators to produce therein ultrasonic vibrations which shape the starting, particulate material to produce a shaped slurry. "Shaped slurry" means herein a slurry of shaped, viz. rounded, near spherical, ground particles.

It is known that the generation of a high frequency, ultrasonic vibration field in liquids results in cavitation and in the production of high local pressures. The high pressure in the cavities, near the particles suspended in the partial solvent, normally produces a grinding effect, sharply reducing the particles size, as is taught in the prior art. Surprisingly it has been found that in the process and apparatus of this invention ultrasonic vibrations in the appropriate liquid produce a shaping effect, imparting to the particles a rounded, near spherical configuration. The shaping is accompanied by a grinding effect, viz. a reduction of the particles size. Whether the shaping or the grinding effect is predominant, depends on the frequency of the vibrations, on the energy density, on the type of the liquid and on the properties of the material, viz. whether it is easy or hard to grind. Higher frequencies increase the shaping effect. While the frequencies used in the method according to the invention are preferably from 20 KHz to 50 KHz, shaping is generally predominant at frequencies above 40 KHz, and grinding is generally predominant at frequencies below 25 KHz. Between 25 KHz and 40 KHz, both effects are present in varying ratios.

The shaped particles can be separated from their slurry by removing the partial solvent, by means appropriate to the particular partial solvent and to the material of the particles, which can include decantation and/or filtration.

By "partial solvent" is meant a liquid, typically water or a liquid comprising or consisting of an organic compound, in which the material to be ground-shaped has a solubility comprised between 1 and 10, wherein the solubility is expressed as grams of material that are dissolved in 100 ml of the liquid at a temperature of 20° C. Examples of such partial solvents are organic solvents such as acetone, methyl ethyl ketone, and mixtures of said solvents with one another or other solvents and/or a minor—less than 10 wt %—amount of water.

Preferably, the partial solvent used should have a boiling point from 40° to 100° C.

It is generally preferred to stir the slurries—both the raw and the shaped slurry—during the shaping operation. Preferably, the stirring speed should be from 100 to 800 rpm. Also preferably the ultrasound energy density should be from 10 to 50 watts/liter.

The method of the invention is generally applicable to the shaping of solid, particulate materials of organic compounds, but preferred embodiments thereof are the shaping of high explosives, solid propellants and pharmaceutical compounds or compositions. Optionally, and particularly if explosives or solid propellants are ground, the method further comprises cooling the slurry during the shaping, to avoid a temperature rise above a safe limit, which depends upon the particular explosive or solid propellant being treated.

The method of the invention can be carried out in batch, semi-batch or continuous operation.

The raw slurry should contain an amount of solid, particulate material from 10 wt % to 75 wt %. The dimensions of the raw particles of the material to be shaped should not exceed 2000 μm.

The apparatus according to the invention comprises a vessel defining a treatment space, having an inlet for the raw slurry and an outlet for the shaped slurry, and generators of ultrasonic vibrations that are preferably distributed about the periphery of the treatment space, viz. the space occupied by the slurry which is being transformed from raw to shaped, in order to obtain an efficient ultrasonic cavitation field, but may be located otherwise and have any suitable shape. Stirring means are provided and assure that the particles of the slurry, as it is so transformed, are uniformly exposed to the ultrasound and a homogeneous product is obtained. The apparatus of the invention may be adapted to carry out the method of the invention in batchwise manner. In any case, the volume of the treatment space, and therefore of the slurry which is subjected to ultrasonic vibrations, is related to the power applied in such a way as to obtain the energy densities hereinbefore specified.

The apparatus preferably comprises stirring means for assuring the homogeneity of the slurry; and cooling means, particularly when the material to be shaped is an explosive or a solid propellant.

The frequency of the ultrasonic vibrations is preferably from 20 to 50 KHz. The power applied through the ultrasonic vibrations is preferably 10 to 50 watts/liter.

The method and apparatus of the invention are not limited to the shaping of any particular solid, particulate material, since and operative parameters of the method and the structure of the apparatus can be adjusted by the skilled person, depending on the nature of the material.

DETAILED DESCRIPTION OF PREFERRED EMBODIMENTS

In the following description, reference is made particularly to explosives, typical examples of which are RDX, HMX and CPX, but this is done only for illustrative purposes, and is not to be construed as a limitation of the invention to the shaping of explosives.

Figure 1:
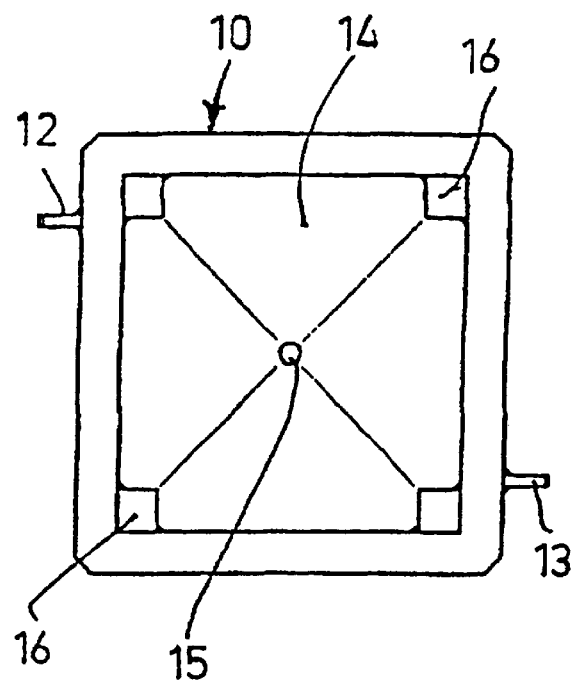
FIG. 1 is a plane view from above of a vessel, which is the part of the apparatus in which the ultrasonic shaping occurs, according to an embodiment of the invention.
Figure 2:
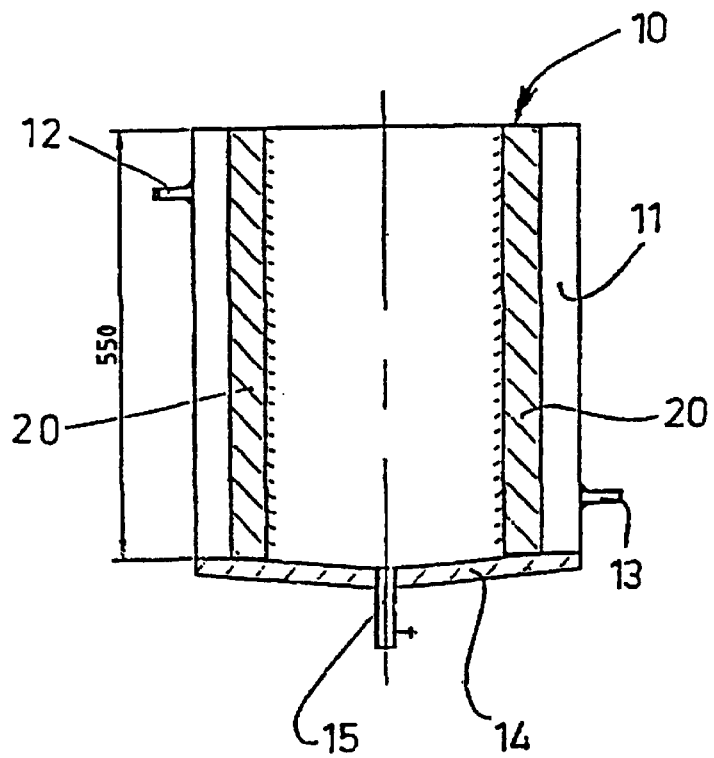
FIG. 2 is an axial cross-section of the vessel of FIG. 1.
Figure 3:
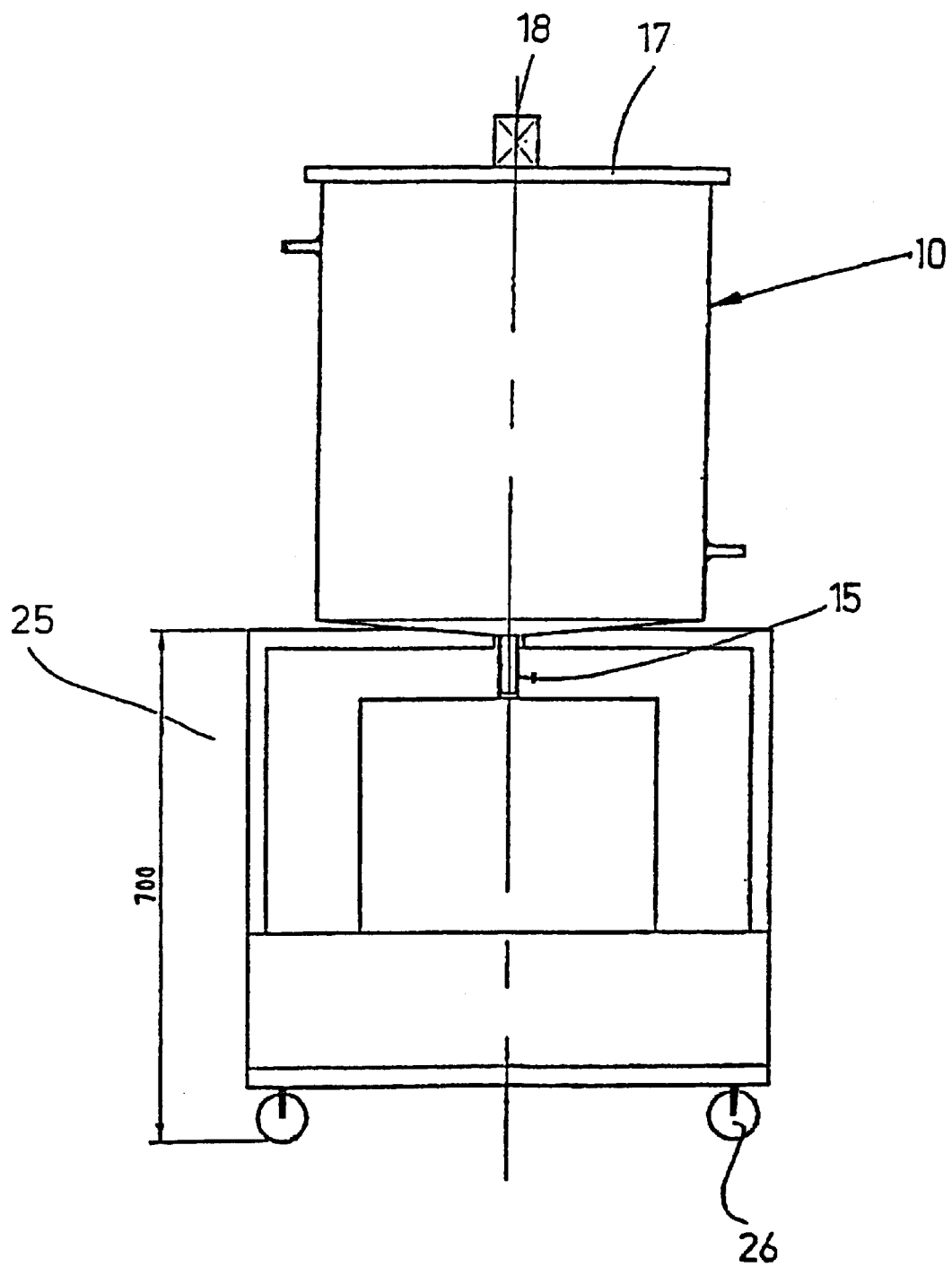
FIG. 3 is a schematic view of the vessel of FIGS. 1 and 2, mounted on a movable container for receiving the shaped slurry.

With reference now to FIGS. 1 and 2, numeral 10 generally designates a cavitation vessel in which the cavitation and the shaping of the slurry occurs and the inside of which constitutes the treatment space. Cavitation vessel 10 is provided with double wall 11, made e.g. of metal sheets, forming a space through which a cooling fluid is introduced through an inlet 12 and discharged through an outlet 13. The cavitation vessel also has a bottom 14, which is slanted to facilitate discharge of the slurry of shaped particles from the latter, and in the center of which a shaped slurry outlet 15 is provided. Numeral 16 designates posts which occupy spaces that are not in the effective zone for the cavitation process, so that if they were filled with liquid, this would not take part in said process. Numeral 20 indicates the ultrasonic generators that will be described later on. The vessel 10 is also provided with a preferably double-walled cover 17 that is visible only in FIG. 3, and which is provided with any suitable attachments for connecting it to vessel 10. Cover 17 supports a motor 18, which actuates a stirrer, not illustrated in the drawings, through an opening for its shaft.

Figure 4:
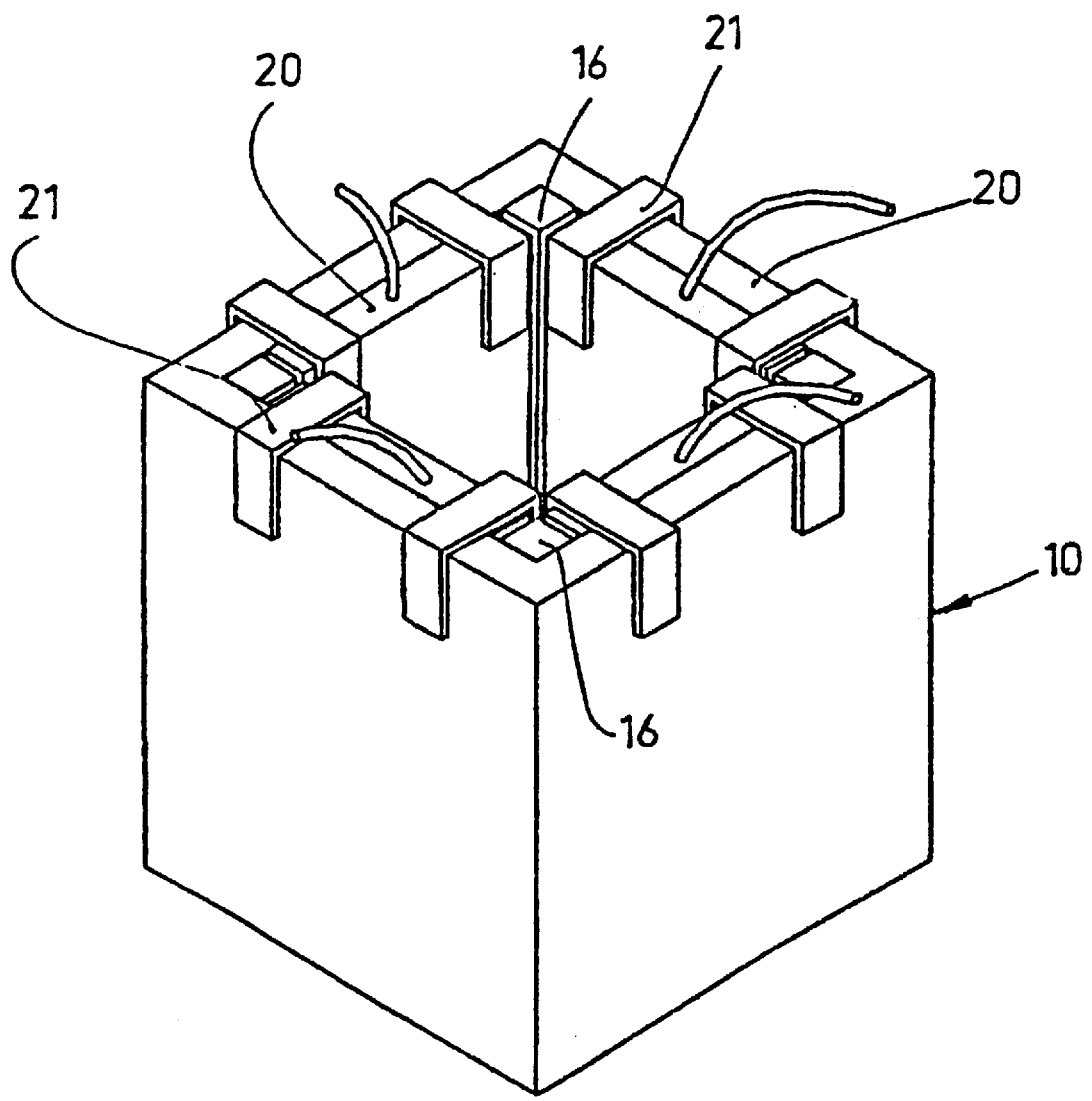
FIG. 4 is a perspective view from above of the vessel of FIGS. 1 and 2, in which the ultrasonic generators have been introduced.
Figure 5:
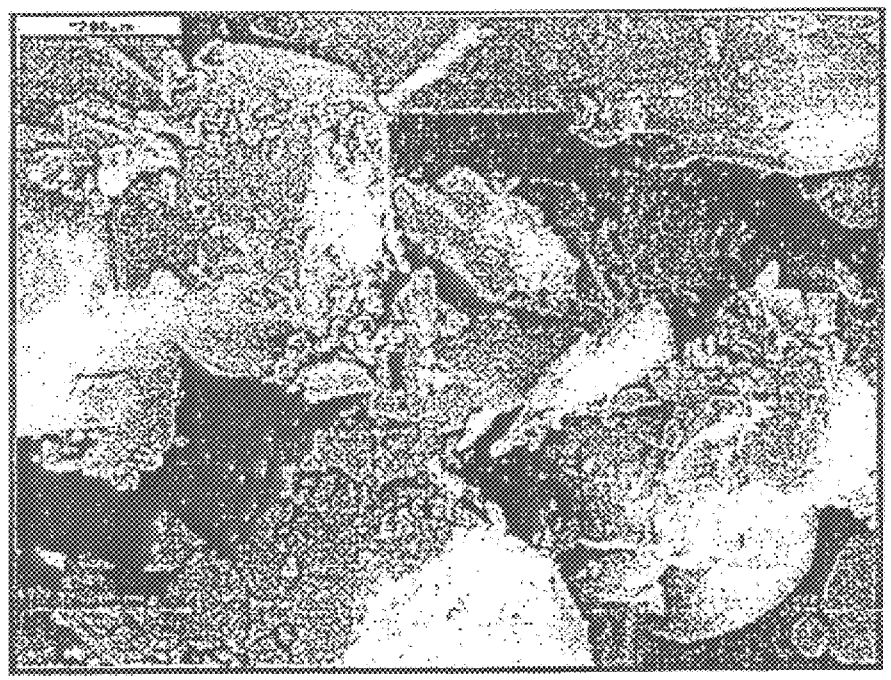
FIGS. 5 and 6 are photographs of RDX and HMX particles, respectively, not treated according to the invention.
Figure 6:
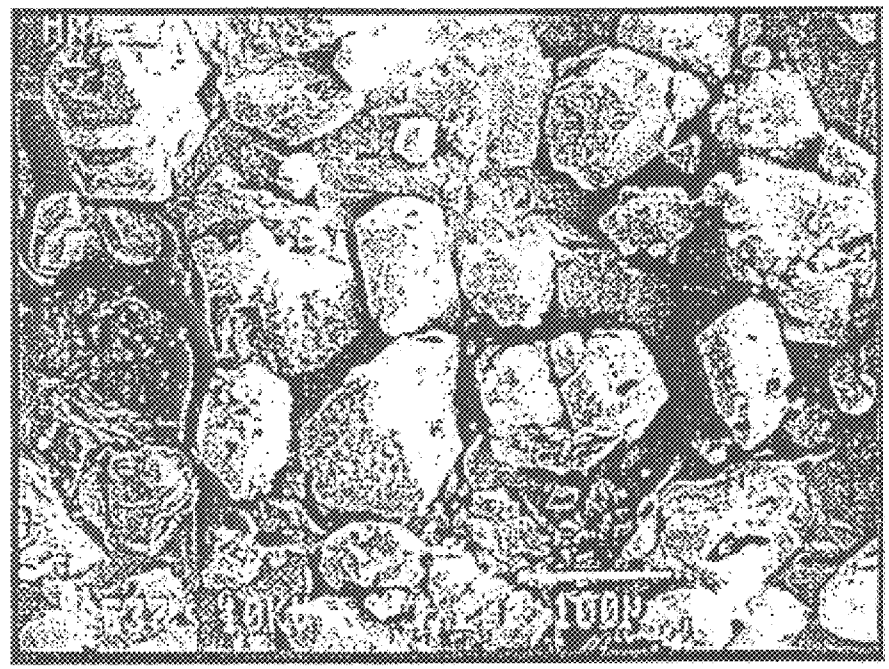
Figure 7:
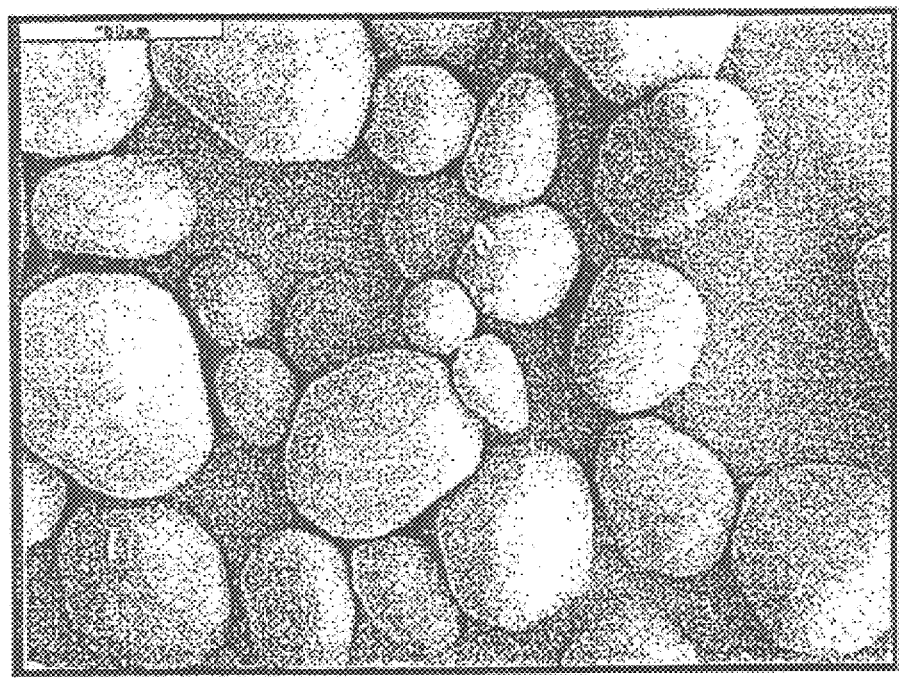
FIGS. 7 and 8 are photographs of RDX and HMX particles, respectively, treated according to the invention.

As seen in FIG. 4, ultrasound generators, or more precisely, the transducers that generate the ultrasound, designated by numeral 20, are mounted by means of hooks 21 on the cavitation vessel 10, so that they almost completely surround the treatment space in which the ultrasonic shaping occurs. The ultrasound generators may be of any type, such as known in the art. The ultrasonic vibrations gradually transform the raw slurry to a shaped slurry.

The cavitation vessel 10 may be conveniently mounted on a receptor container 25, into which the slurry of the ground particles is emptied after the shaping has been terminated. The receptor container 25 can be mounted, if desired, on wheels 26, to make it mobile.

Figure 8:
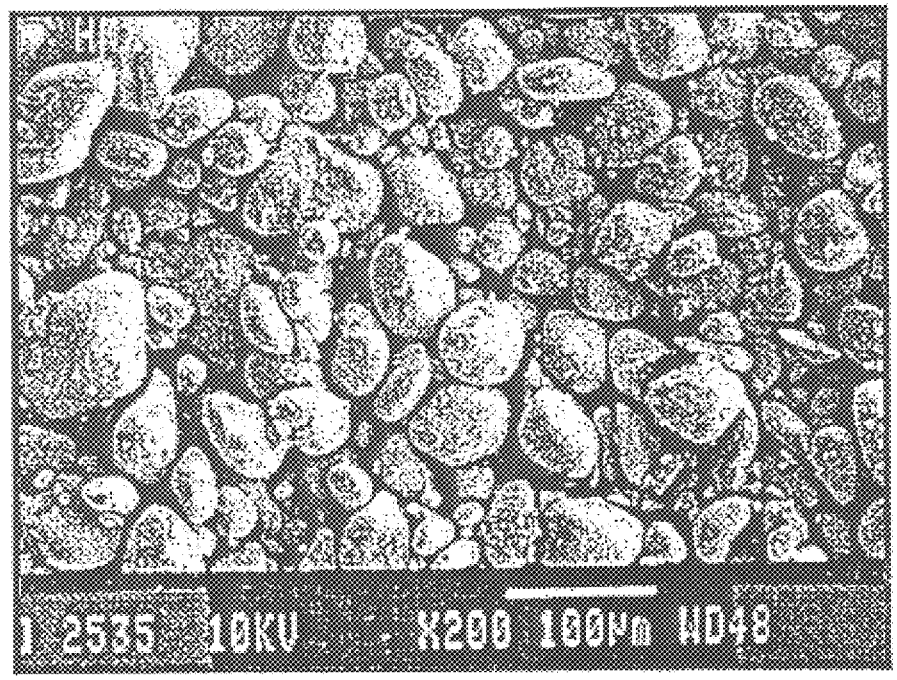

FIGS. 5 to 8 are photographs of RDX and HMX particles illustrating the shaping effect of an embodiment of the invention. A comparison of FIG. 5 with FIG. 7 and of FIG. 6 with FIG. 8 shows that the treatment of the invention has produced mostly well rounded particles from raw particles that had shapes from very angular to sub-angular. The following are non-limitative examples of embodiments of the invention.

EXAMPLE 1

Production of rounded HMX particles in the size of 60 $\mu$m 1500 gr of fine HMX are suspended in 3000 ml of technical acetone and are stirred for 4 hours, while subjecting the suspension to ultrasound vibration having a frequency of 40 KHz. The stirring speed is 180 rpm and the energy density of the ultrasound is 50 watts/liter.

EXAMPLE 2

Production of rounded RDX in the size of 150 $\mu$m 50 gr of coarse RDX are suspended in 100 ml ethanol and stirred for 1.5 hours, while subjecting the suspension to ultrasound vibration having a frequency of 25 KHz. The stirring speed is 150 rpm and the energy density of the ultrasound is 10 watts/liter.

While embodiments of the invention have been described by way of illustration, it will be understood that the invention can be carried out with many modifications, variations and adaptations, without departing from its spirit or exceeding the scope of the claims.

What is claimed is:

1. A method of shaping starting solid, particulate materials comprising suspending said starting material in a liquid which is a partial solvent for said starting material to form a starting suspension, and applying ultrasonic vibrations to said starting suspension, whereby said starting material is shaped and ground to produce a final suspension of ground and rounded particles.

2. A method according to claim 1, further comprising separating said ground and shaped particles from said final suspension by removing said partial solvent.

3. A method according to claim 2, wherein said partial solvent is removed by decantation or filtration.

4. A method according to claim 2, wherein said partial solvent is a liquid in which said starting material to be shaped has a solubility between 1 and 10, wherein said solubility is expressed as grams of material that are dissolved in 100 ml of said liquid at a temperature of 20° C.

5. A method according to claim 1, wherein said partial solvent is an organic solvent.

6. A method according to claim 1, wherein said partial solvent is selected from the group consisting of acetone, methyl ethyl ketone, and mixtures thereof.

7. A method according to claim 6 wherein said partial solvent is mixed with a minor amount of water.

8. A method according to claim 5, wherein said partial solvent has a boiling point from 40° to 100° C.

9. A method according to claim 1, further comprising stirring said starting suspension during the application of said ultrasonic vibrations.

10. A method according to claim 9, further comprising cooling said starting suspension during said shaping.

11. A method according to claim 1, wherein said starting material comprises high explosives or solid propellants.

12. A method according to claim 1, wherein said starting material comprises pharmaceutical compounds or compositions.

13. A method according to claim 1, wherein said starting material comprises high cost organic materials.

14. A method according to claim 1, wherein said starting suspension of said starting solid, particulate material contains an amount of said starting material from 10 wt % to 75 wt %.

15. A method according to claim 1, wherein said starting material has particles of dimensions which do not exceed 2000 $\mu$m.

16. A method according to claim 1, wherein said ultrasonic vibrations have a frequency from 20 to 50 KHz.

17. A method according to claim 1, wherein said ultrasonic vibrations have an energy density from 10 to 50 watts/liter.

* * * * *

UNITED STATES PATENT AND TRADEMARK OFFICE
CERTIFICATE OF CORRECTION

PATENT NO.    : 6,669,122 B2
DATED         : Decmeber 30,2003
INVENTOR(S)   : Tamar Kaully et al.

It is certified that error appears in the above-identified patent and that said Letters Patent is hereby corrected as shown below:

Column 3,
Line 6, cancel the comma "," (first occurrence).

Column 4,
Line 20, delete "of".
Line 20, delete "a" (second occurrence) and in place thereof insert -- the --.

Column 5,
Line 44, after "starting" add -- solid --.
Line 45, after "starting" add -- solid --.
Line 46, after "suspension," add -- comprising said starting solid material and said partial solvent --.
Line 47, after "starting" (second occurrence) add -- solid --.

Signed and Sealed this

Sixth Day of April, 2004

JON W. DUDAS
*Acting Director of the United States Patent and Trademark Office*